(12) United States Patent
Honda

(10) Patent No.: US 9,157,899 B2
(45) Date of Patent: Oct. 13, 2015

(54) PURIFYING AGENT FOR OILY LIQUID CONTAINING POLYCHLORINATED BIPHENYLS

(75) Inventor: Katsuhisa Honda, Matsuyama (JP)

(73) Assignees: EHIME UNIVERSITY, Ehime (JP); MIURA CO., LTD., Ehime (JP)

( * ) Notice: Subject to any disclaimer, the term of this patent is extended or adjusted under 35 U.S.C. 154(b) by 664 days.

(21) Appl. No.: 13/123,903

(22) PCT Filed: Oct. 26, 2009

(86) PCT No.: PCT/JP2009/068739
§ 371 (c)(1),
(2), (4) Date: Apr. 13, 2011

(87) PCT Pub. No.: WO2010/073818
PCT Pub. Date: Jul. 1, 2010

(65) Prior Publication Data
US 2011/0198291 A1    Aug. 18, 2011

(30) Foreign Application Priority Data

Dec. 25, 2008 (JP) .................................. 2008-329441

(51) Int. Cl.
*G01N 30/14* (2006.01)
*B01J 20/10* (2006.01)
(Continued)

(52) U.S. Cl.
CPC ............... *G01N 30/14* (2013.01); *B01J 20/103* (2013.01); *B01J 20/28047* (2013.01);
(Continued)

(58) Field of Classification Search
CPC ............... B01J 20/103; B01J 20/28047; B01J 20/28052; B01J 20/3204; B01J 20/3236;
G01N 1/34; G01N 30/14; G01N 33/2835; G01N 2030/8854; G01N 30/7206; G01N 2030/884; G01N 2030/8872
USPC ............................ 210/635, 656, 198.2, 502.1
See application file for complete search history.

(56) References Cited

U.S. PATENT DOCUMENTS 1,547,236 A * 7/1925 Reyerson ...................... 502/240
1,935,188 A * 11/1933 Latshaw et al. ............... 502/262
(Continued)

FOREIGN PATENT DOCUMENTS

CN    101105477 A    1/2008
EP    1 612 552 A1    1/2006
(Continued)

OTHER PUBLICATIONS

PTO Translation No. 11-2192 of JP 2001330598 dated Feb. 2011.*
(Continued)

*Primary Examiner* — Ernest G Therkorn
(74) *Attorney, Agent, or Firm* — Birch Stewart Kolasch & Birch, LLP

(57) ABSTRACT

A column 1 for removing an interfering substance to an analysis of polychlorinated biphenyls contained in an oily liquid such as an electric insulating oil from the oily liquid, includes a first column 10 packed with a multilayer silica gel 13 in which an upper layer 14 of a sulfuric acid silica gel is stacked on a lower layer 15 of a nitrate silica gel and a second column 20 connected to the lower layer 15 side of the column 10 and packed with an alumina layer 23. The nitrate silica gel of the lower layer 15 is produced by treating an activated silica gel with a mixed aqueous solution of copper nitrate and silver nitrate, wherein the ratio by mole of the copper element to the silver element (the copper element:the silver element) is preferably from 1:0.5 to 2.0.

10 Claims, 14 Drawing Sheets

(51) Int. Cl.
  *B01J 20/28* (2006.01)
  *B01J 20/32* (2006.01)
  *G01N 1/34* (2006.01)
  *G01N 33/28* (2006.01)
  *G01N 30/72* (2006.01)
  *G01N 30/88* (2006.01)

(52) U.S. Cl.
  CPC ....... *B01J 20/28052* (2013.01); *B01J 20/3204* (2013.01); *B01J 20/3236* (2013.01); *G01N 1/34* (2013.01); *G01N 33/2835* (2013.01); *G01N 30/7206* (2013.01); *G01N 2030/884* (2013.01); *G01N 2030/8854* (2013.01)

(56) References Cited

U.S. PATENT DOCUMENTS

| | | | | |
|---|---|---|---|---|
| 3,900,425 | A * | 8/1975 | Robinson | 502/159 |
| 4,431,546 | A * | 2/1984 | Hughes et al. | 210/656 |
| 4,648,975 | A * | 3/1987 | Barkatt et al. | 210/656 |
| 6,297,191 | B1 * | 10/2001 | Puranik et al. | 502/401 |
| 6,316,647 | B1 * | 11/2001 | Ohtsu et al. | 554/194 |
| 2004/0007513 | A1 * | 1/2004 | Kanehara et al. | 210/198.2 |
| 2005/0287037 | A1 * | 12/2005 | Honda et al. | 422/62 |
| 2007/0245928 | A1 * | 10/2007 | Bennert et al. | 106/287.17 |
| 2009/0107213 | A1 * | 4/2009 | Honda et al. | 73/23.37 |
| 2010/0116023 | A1 * | 5/2010 | Honda et al. | 73/23.41 |
| 2011/0049056 | A1 * | 3/2011 | Wyndham et al. | 210/656 |

FOREIGN PATENT DOCUMENTS

| | | | |
|---|---|---|---|
| EP | 2136196 | * | 12/2009 |
| EP | 2136196 A1 | | 12/2009 |
| JP | 6-135895 A | | 5/1994 |
| JP | 2001-330598 A | | 11/2001 |
| JP | 2002-181673 A | | 6/2002 |
| WO | WO 2008/123393 A1 | | 10/2008 |

OTHER PUBLICATIONS

PTO Translation No. 12-1830 of JP 2002181673 dated Feb. 2012.*
PTO Translation No. 14-5890 of Japan Patent No. 06135895 Sep. 2014.*
"Method of Testing Standards Concerned with General Wastes Subject to Special Control and Industrial Waste Subject to Special Control", Ministry of Health and Welfare of Japan, Appendix No. 2 in Announcement No. 192, 1992, pp. 357-361.
International Search Report dated Jan. 19, 2010 for International Application No. PCT/JP2009/068739.
European Search Report dated Aug. 7, 2012 of Application No. 09 83 4622.

* cited by examiner

PURIFYING AGENT FOR OILY LIQUID CONTAINING POLYCHLORINATED BIPHENYLS

REFERENCE TO RELATED APPLICATIONS

This application is a 371 of PCT/JP2009/068739 filed Oct. 26, 2009.

TECHNICAL FIELD

The present invention relates to a purifying agent for an oily liquid containing polychlorinated biphenyls, in particular, a purifying agent for removing, from an oily liquid, an interfering substance to an analysis of polychlorinated biphenyls contained in the oily liquid.

BACKGROUND ART

As electric insulating oils for electrical instruments such as transformers or capacitors, those made of mineral oils containing polychlorinated biphenyls (hereinafter referred to as "PCBs" as the case may be) excellent in electric insulation properties were generally used. However, the toxicity of PCBs to the living body has been confirmed, so that in Japan, the production and import of PCBs have already been prohibited, and use of electric insulating oils and the like that contain PCBs came to be substantially prohibited. However, as it was feared that PCB-containing electric insulating oils and the like that were used in the past may cause environmental pollution in their disposal process, electrical instrument manufacturers or users, industrial waste disposers, and others have been continuing to store the oils and the like, as they are, over a long term up to the present time.

Meanwhile, with the background of the establishment of a safe process for chemically decomposing PCBs, in Japan the so-called PCB special measures law was enacted in 2001. This law obliges to dispose of all PCBs wastes which have been hitherto used or stored, typical examples of which include PCBs-containing electric insulating oils, by July in 2016.

It was initially assumed that PCBs wastes that should be disposed of under the PCB Special Measures Law were limited to those electric insulating oils and the like which had been manufactured or used until production and use of PCBs were prohibited and which had been stored heretofore. However, there were cases where PCBs estimated to be mixed during the production process were detected in electric insulating oils and the like manufactured after prohibition of use of PCBs, and thus some electric insulating oils used at present in electric instruments such as transformers may correspond to PCBs wastes subject to the PCB Special Measures Law. The PCB Special Measures Law set out the time limit as described above, so there has been demand for promptly judging whether electric insulating oils used in existing electric instruments and the like correspond to the PCBs wastes subject to the PCB Special Measures Law (that is, oils and the like containing PCBs at a concentration of not less than 0.5 mg/kg correspond to the PCBs wastes subject to the PCB Special Measures Law, and judgment of whether oils and the like correspond to the PCBs wastes or not is referred to as PCB screening).

It is usually judged based on a result obtained by a high-sensitivity analysis, such as gas chromatography or bioassay, whether or not a sample collected from an object such as an electric insulating oil, contains PCBs at a predetermined concentration. Thus, the sample needs to be subjected to a high-level pretreatment for removing any interfering substance producing an effect on analysis results. Such a pretreatment is usually conducted in accordance with a method described in Appendix No. 2 in Announcement No. 192 issued in 1992 by the Ministry of Health and Welfare of Japan "Method of Testing Standards Concerned with General Wastes Subject to Special Control and Industrial Waste Subject to Special Control" (hereinafter referred to as the "official method"). However, the official method needs a complicated treatment having many steps, such as dimethylsulfoxide (DMSO)/hexane partition, a sulfuric acid treatment, an alkali treatment, and a silica gel column treatment; thus, in order to complete the method, a long period, the length of which is specified by day, is required, and further costs for conducting the method are also very high.

Thus, investigations have been made about a method for pretreating an object to be judged in place of the official method. As a method of extracting polychlorinated biphenyls from an oily liquid such as an electric insulating oil containing PCBs by a simple operation in a short period in order to prepare a sample for analysis, the pamphlet of International Publication WO 2008/123393 discloses a method using a column into which a sulfuric acid silica gel, a metal salt hydrate silica gel (for example, a copper salt hydrate silica gel), a silver nitrate silica gel, and alumina are filled.

However, the metal salt hydrate silica gel or silver nitrate silica gel used in this pretreatment method deteriorates, with the passage of time, after the preparation thereof, so that the capability thereof for removing interfering substances contained in an oily liquid tends to lower. Thus, analysis results of a sample obtained by this pretreatment method may be affected by the interfering substances which remain in the sample.

An object of the present invention is to enhance the level of pretreatment of an oily liquid for which polychlorinated biphenyls contained therein are analyzed.

DISCLOSURE OF THE INVENTION

The present invention relates to a purifying agent for an oily liquid containing polychlorinated biphenyls, which is for removing, from the oily liquid, an interfering substance to an analysis of polychlorinated biphenyls contained in the oily liquid. This purifying agent contains a nitrate silica gel yielded by treating an activated silica gel with a mixed aqueous solution of copper nitrate and silver nitrate.

This purifying agent does not exhibit the capability of adsorbing polychlorinated biphenyls while the agent exhibits an excellent capability of adsorbing an interfering substance which affects an effect on an analysis of the polychlorinated biphenyls contained in the oily liquid, and a decomposition product thereof; thus, the interfering substance can be effectively separated from the polychlorinated biphenyls contained in the oily liquid. This function hardly deteriorates even when a time elapses after the preparation of the purifying agent. Thus, when this purifying agent is used for a pretreatment of the oily liquid containing the polychlorinated biphenyls to prepare a sample for analyzing the polychlorinated biphenyls, the analytical accuracy of the polychlorinated biphenyls contained in the oily liquid can be improved.

Another aspect of the present invention relates to a purifying column for an oily liquid containing polychlorinated biphenyls, which is for removing, from the oily liquid, an interfering substance to an analysis of polychlorinated biphenyls contained in the oily liquid. The column includes a first layer of a sulfuric acid silica gel, and a second layer of a purifying agent containing a nitrate silica gel yielded by treating an activated silica gel with a mixed aqueous solution of copper nitrate and silver nitrate, arranged below the first layer.

In this purifying column, the oily liquid is added into the sulfuric acid silica gel of the first layer so as to be penetrated into the gel while the gel is heated. In this state, when the gel is kept for a predetermined time, the interfering substance contained in the oily liquid can be at least partially decomposed. Moreover, the first layer exhibits a strong dehydrating action. Accordingly, the first layer decomposes the interfering substance contained in the oily liquid at least partially, and further can effectively absorb water incorporated in the oily liquid.

Thereafter, an aliphatic hydrocarbon solvent is supplied into the first layer side and this aliphatic hydrocarbon is developed from the first layer to the second layer. In this way, the aliphatic hydrocarbon solvent dissolves the interfering substance which remains in the first layer, the decomposition products generated in the first layer, the polychlorinated biphenyls and the oily liquid, so that these components are transferred into the second layer. Since the second layer is made of the purifying agent of the present invention, the second layer adsorbs the interfering substance and the decomposition products therefrom from the first layer, and allows the oily liquid and the polychlorinated biphenyls together with the aliphatic hydrocarbon solvent to be passed therethrough. In this way, the polychlorinated biphenyls are separated from the interfering substance. This function of the second layer hardly deteriorates even when a time elapses after the preparation of the purifying agent; thus, when the purifying column of the present invention is used to treat the oily liquid, the interfering substance contained in the oily liquid can be effectively separated from the polychlorinated biphenyls therein. It is therefore possible to prepare a sample for analyzing the polychlorinated biphenyls that is excellent in enhancing the analytical accuracy.

In the purifying column of the present invention, the first layer and the second layer may be filled into the same column. Alternatively, the purifying column of the present invention may include a forward column with which the first layer is packed, and a backward column with which the second layer is packed, wherein the forward column and the backward column are connected to each other so as to be separable from each other.

Still another aspect of the present invention relates to a column for separating polychlorinated biphenyls from an oily liquid containing the polychlorinated biphenyls in order to analyze the polychlorinated biphenyls. This column includes a first column and a second column. The first column includes a first layer of a sulfuric acid silica gel, and a second layer of a purifying agent containing a nitrate silica gel yielded by treating an activated silica gel with a mixed aqueous solution of copper nitrate and silver nitrate, arranged below the first layer. The second column is packed with alumina and attachable to and detachable from the second layer side of the first column.

The first column of this separating column corresponds to the purifying column of the present invention, and as described above, can separate an interfering substance contained in the oily liquid effectively from the polychlorinated biphenyls contained in the oily liquid.

In the meantime, when an aliphatic hydrocarbon solvent containing the polychlorinated biphenyls and the oily liquid passed through the second layer of the first column is supplied into the second column, the second column captures the polychlorinated biphenyls by its alumina. Thus, the second column allows the oily liquid together with the aliphatic hydrocarbon solvent to be passed therethrough. As a result, the polychlorinated biphenyls are separated from the oily liquid.

When an extracting solvent in which the polychlorinated biphenyls can be dissolved is supplied to the second column and passed therethrough, the polychlorinated biphenyls captured in the second column can be secured as a solution of the extracting solvent. This solution is usable as a sample for analyzing the polychlorinated biphenyls.

The first column of the separating column of the present invention may be a single column with which the first layer and the second layer are packed. Alternatively, the first column includes a forward column with which the first layer is packed, and a backward column with which the second layer is packed, wherein the forward column and the backward column are connected to each other so as to be separable from each other.

A further aspect of the present invention relates to a method for extracting polychlorinated biphenyls from an oily liquid containing the polychlorinated biphenyls. This extracting method includes the steps of adding the oily liquid to a sulfuric acid silica gel layer; allowing the sulfuric acid silica gel layer to which the oily liquid is added to be kept in a state heated to at least 35° C. for a predetermined period and then cooling the layer to ordinary temperature; supplying an aliphatic hydrocarbon solvent to the sulfuric acid silica gel layer cooled to ordinary temperature; allowing the aliphatic hydrocarbon solvent passed through the sulfuric acid silica gel layer to be supplied to, and passed through, a nitrate silica gel layer; allowing the aliphatic hydrocarbon solvent passed through the nitrate silica gel layer to be supplied to, and passed through, an alumina layer; allowing an extracting solvent capable of dissolving the polychlorinated biphenyls to be supplied to, and passed through, the alumina layer; and securing the extracting solvent passed through the alumina layer. The nitrate silica gel layer used in this extracting process contains a nitrate silica gel yielded by treating an activated silica gel with a mixed aqueous solution of copper nitrate and silver nitrate.

In this extracting process, when the a sulfuric acid silica gel layer to which an oily liquid is added is allowed to be kept in a state heated to at least 35° C. for a predetermined period, any interfering substance contained in the oily liquid, which affects an analysis of the polychlorinated biphenyls contained in the oily liquid, in particular, an aromatic compound reacts at least partially with the sulfuric acid silica gel layer so as to be promptly decomposed. The resulting decomposition products, together with the polychlorinated biphenyls and any undecomposed interfering substance (mainly any paraffin in a case where the oily liquid is, for example, an electric insulating oil made of a mineral oil), are held in the sulfuric acid silica gel layer. Then, when the sulfuric acid silica gel layer cooled to ordinary temperature is supplied with an aliphatic hydrocarbon solvent, the aliphatic hydrocarbon solvent passes through the sulfuric acid silica gel layer to be supplied to a nitrite silica gel layer, and then passes through the nitrate silica gel layer. At this time, the polychlorinated biphenyls, a part of the decomposition products, the undecomposed interfering substance, and the oily liquid which are each held in the sulfuric acid silica gel layer are dissolved in the aliphatic hydrocarbon solvent supplied to the sulfuric acid silica gel layer, so as to be supplied from the sulfuric acid silica gel layer to the nitrate silica gel layer. The decomposition products and the undecomposed interfering substance each contained in the aliphatic hydrocarbon solvent supplied to the nitrate silica gel layer are adsorbed and held onto the nitrate silica gel layer. By contrast, the polychlorinated biphenyls and the oily liquid each contained in the aliphatic hydrocarbon solvent supplied to the nitrate silica gel layer pass through the nitrate silica gel layer in the state of being dissolved in the aliphatic hydrocarbon solvent. As a result, the polychlorinated biphenyls are separated from the interfering substance.

Next, when the aliphatic hydrocarbon solvent passed through the nitrate silica gel layer, that is, the aliphatic hydrocarbon solvent in which the polychlorinated biphenyls and the oily liquid are dissolved is supplied to and passed through the alumina layer, the polychlorinated biphenyls dissolved in the aliphatic hydrocarbon solvent are captured by the alumina layer while the oily liquid dissolved in the aliphatic hydrocarbon solvent, together with the aliphatic hydrocarbon solvent, passes through the alumina layer. When the extracting solvent is supplied to, and passed through the alumina layer, the polychlorinated biphenyls captured by the alumina layer are dissolved in the extracting solvent, and extracted from the alumina layer to be secured as a solution of the extracting solvent.

According to this extracting process, therefore, high-purity polychlorinated biphenyls, from which an interfering substance has been removed, can be extracted from a polychlorinated biphenyls-containing oily liquid in a shorter time by a simple operation.

An additional aspect of the present invention relates to a method for analyzing polychlorinated biphenyls in an oily liquid containing the polychlorinated biphenyls. This analyzing method includes the steps of adding a sample collected from the oily liquid to a sulfuric acid silica gel layer; allowing the sulfuric acid silica gel layer to which the sample is added to be kept in the state heated to at least 35° C. for a predetermined period, and then cooling the layer to ordinary temperature; supplying an aliphatic hydrocarbon solvent to the sulfuric acid silica gel layer cooled to ordinary temperature; allowing the aliphatic hydrocarbon solvent passed through the sulfuric acid silica gel layer to be supplied to, and passed through, a nitrate silica gel layer; allowing the aliphatic hydrocarbon solvent passed through the nitrate silica gel layer to be supplied to, and passed through, an alumina layer; allowing an extracting solvent capable of dissolving polychlorinated biphenyls to be supplied to, and passed through, the alumina layer; securing the extracting solvent passed through the alumina layer; and analyzing the secured extracting solvent by either one among gas chromatographic method and bioassay technique. The nitrate silica gel layer used in this analyzing method contains a nitrate silica gel yielded by treating an activated silica gel with a mixed aqueous solution of copper nitrate and silver nitrate.

This analyzing method is that in which the solution of the extracting solvent secured by the above-mentioned extracting process according to the present invention is analyzed by either one among chromatographic method and bioassay technique. The secured solution of the extracting solvent may be applied to an analysis by either gas chromatographic method or bioassay technique directly, or after being suitably concentrated.

According to this analyzing method, it is possible to prepare, from a sample of an oily liquid containing polychlorinated biphenyls, a high-purity analyzing sample of the polychlorinated biphenyls, from which an interfering substance has been removed, in a shorter time by a simple operation. For this reason, the polychlorinated biphenyls in the oily liquid can be rapidly analyzed with high accuracy by gas chromatographic method or bioassay technique.

The gas chromatographic method used in this analyzing process is a technique suitable for analysis of a trace amount of polychlorinated biphenyls and is usually preferably one technique selected from gas chromatography-mass spectrometry and gas chromatography-electron capture detection. The bioassay technique used in this analyzing process is preferably an Ah receptor binding assay technique or an immunoassay technique using an anti-polychlorinated-biphenyls antibody.

In the extracting method and the analyzing method of the present invention, the sulfuric acid silica gel layer, the nitrate silica gel layer, and the alumina layer are not particularly limited about the use form thereof. The layers may be used in the state of being filled into a column, or of being arranged in an appropriate filtrating tool. It is usually preferred to use the layers in the state of being filled into a column. A preferred example of the column with which the sulfuric acid silica gel layer, the nitrate silica gel and the alumina layer are packed is that wherein the sulfuric acid silica gel layer and the nitrate silica gel layer are stacked and packed in a single column, and the alumina layer is packed in another column attachable to and detachable from the nitrate silica gel layer side of the other column. Another preferred example of the column is that wherein columns with which the sulfuric acid silica gel layer, the nitrate silica gel layer and the alumina layer are packed, respectively, are individually prepared, and these columns are connected to each other in this order so as to be attached to and detached from each other.

In the extracting method and analyzing method of the present invention, the direction in which the extracting solvent is supplied to the alumina layer can be set arbitrarily. Specifically, the direction in which the extracting solvent is supplied to the alumina layer may be set at the same or opposite direction in which the aliphatic hydrocarbon solvent is passed. However, in the case of the above-described preferred column in which the alumina layer is packed with one of columns, the extracting solvent is supplied to and passed through the alumina layer, preferably in a direction opposite to the direction in which the aliphatic hydrocarbon solvent is passed. In the alumina layer, the polychlorinated biphenyls are captured mainly at the end on the supply side of the aliphatic hydrocarbon solvent. Thus, when an extracting solvent is supplied to the alumina layer in a direction opposite to the direction in which the aliphatic hydrocarbon solvent is passed, the polychlorinated biphenyls captured by the alumina layer are rapidly extracted from the alumina layer with a small amount of the extracting solvent. In this case, therefore, the extracting solvent solution of the polychlorinated biphenyls which is obtainable by supplying the extracting solvent to the alumina layer can turn into so small that the solution can be easily applied to an analysis of the polychlorinated biphenyls according to gas chromatographic method or bioassay technique.

In the purifying agent of the present invention, the purifying agents used in the purifying column and the separating column of the present invention, respectively, and the purifying agents used in the extracting method and the analyzing method of the present invention, respectively, the nitrate silica gel is preferably a gel wherein the ratio by mole of the copper element to the silver element (the copper element:the silver element) is from 1:0.5 to 2.0.

Other objects and results the present invention will be described in the following detailed description.

BEST MODE FOR CARRYING OUT THE INVENTION

In the case of analyzing PCBs contained in an oily liquid qualitatively or quantitatively, the purifying agent of the present invention is used to remove, from the oily liquid, an interfering substance which affects the analysis.

Hereinafter, embodiments of the present invention will be described mainly about a method of extracting PCBs from an oily liquid in order to analyze the PCBs contained in the oily liquid.

In the present invention, examples of an oily liquid from which PCBs are to be extracted, that is, an oily liquid containing PCBs include electric insulating oils used in electrical instruments such as transformers and capacitors, PCB-containing organic solvent wastes generated in chemical experiments or chemical factories, extracts for analysis which are each obtained by extracting PCBs from a PCB-containing sample with an organic solvent, and decomposition process liquids or washing liquids generated in facilities for subjecting PCBs to a decomposition treatment. The electric insulating oils are usually composed of mineral oils consisting primarily of paraffin having relatively high boiling point, naphthene, aromatic compounds or the like obtained by rectifying petroleum and may contain PCBs when PCBs are added to improve electric insulation properties or when PCBs are mixed in a production process.

For reference, PCBs are compounds including homologues having 1 to 10 chlorine atoms. However, PCBs contained in the electric insulating oils mentioned above are usually compounds having 2 to 8 chlorine atoms.

Figure 1:
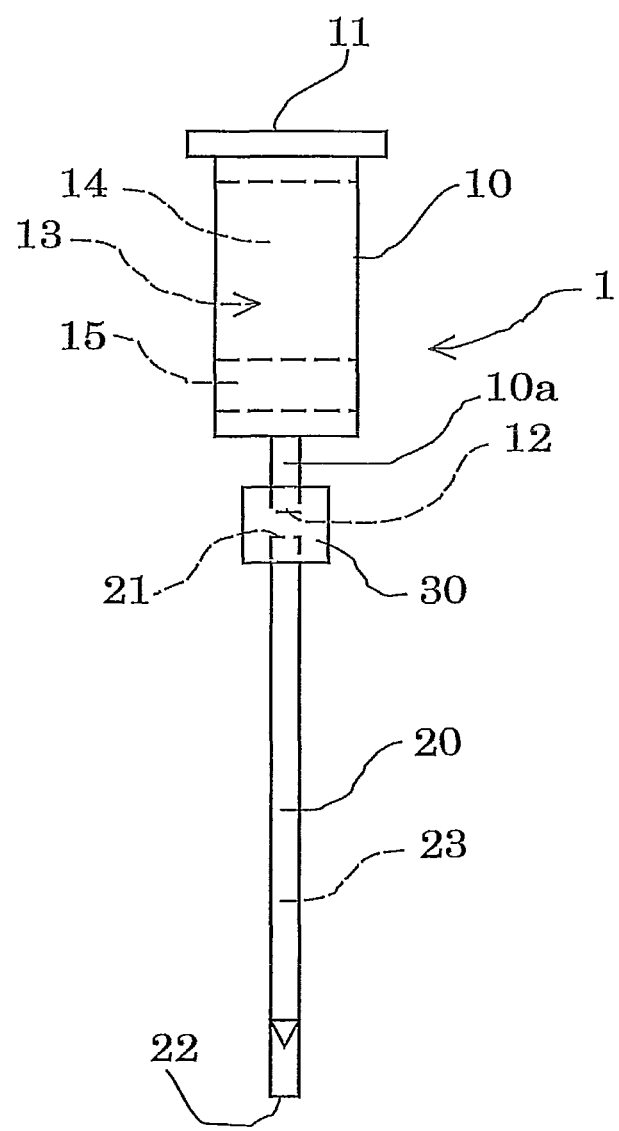
FIG. 1 is a schematic diagram of an example of the column usable in a process for extracting PCBs according to the present invention.

With reference to FIG. 1, a description is made about an example of a column used to carry out a process for extracting PCBs according to the present invention. In the drawing, a column 1 is provided mainly with a first column 10, a second column 20, and a connecting member 30 for connecting the columns 10 and 20 to each other.

The first column 10 is formed in a cylindrical shape with the lower end 10a contracted in outside diameter and inside diameter, and has openings 11 and 12 at the upper and lower ends, respectively. The first column 10 is made of, for example, glass, or a plastic having solvent-resistance, chemical-resistance and heat-resistance. The inside of the first column 10 is packed with a multilayer silica gel 13. The multilayer silica gel 13 has an upper layer 14 stacked on a lower layer 15.

The upper layer 14 is a layer filled with a sulfuric acid silica gel, that is, a sulfuric acid silica gel layer. The sulfuric acid silica gel used herein is prepared by adding concentrated sulfuric acid uniformly to the surface of activated silica gel, and then drying the activated silica gel. The activated silica gel used herein is usually a gel activated by heating a silica gel. Usually, the amount of concentrated sulfuric acid to be added to the activated silica gel is preferably from 10 to 130% by weight of the activated silica gel.

The lower layer 15 is a layer filled with a purifying agent of the present invention. The purifying agent contains a nitrate silica gel yielded by treating an activated silica gel with a mixed aqueous solution of copper nitrate and silver nitrate. Copper nitrate used herein may be a hydrate, for example, a trihydrate, a hexahydrate or a nonahydrate thereof. Usually, it is preferred to use a trihydrate thereof.

The nitrate silica gel may be prepared by adding the above-mentioned mixed aqueous solution uniformly to the surface of an activated silica gel, and then drying the activated silica gel. The mixed aqueous solution is a solution prepared by adding copper nitrate and silver nitrate to purified water such as distilled water and dissolving the nitrates therein. It is usually preferred to use a solution about which at the time of adding the whole amount thereof to the activated silica gel, the respective weights of copper and silver nitrates become 5 to 50% of the weight of the activated silica gel. When a copper nitrate hydrate is used, the amount thereof to be used is determined based on the weight excluding the weight of the hydrated water.

About the mixed aqueous solution, the addition ratio between copper nitrate and silver nitrate therein is adjusted to set the ratio by mole of the copper element to the silver element (the copper element:the silver element) in the nitrate silica gel preferably into the range of 1:0.5 to 2.0, more preferably into the range of 1:0.8 to 1.5. The nitrate silica gel generally hardly deteriorates with the passage of time. However, when the ratio of the copper element to the silver element is adjusted in the above range, chemical stability of free water and semi-bonded water therein is enhanced so that the nitrate silica gel can easily keep water of appropriate amount, and additionally, the nitrate silica gel easily keep bonding forces of nitrate ions therein into an appropriate degree. Thus, the deterioration based on the passage of time is less likely to be caused.

In the multilayer silica gel 13, the ratio by weight of the upper layer 14 to the lower layer 15 (the upper layer 14:the lower layer 15) is desirably set into the range of 2 to 5:1. If the proportion of the upper layer 14 is less than this proportion, the purity of PCBs extracted from an oily liquid falls so that the reliability of analysis results thereof may be damaged. By contrast, if the proportion of the upper layer 14 is more than this proportion, the multilayer silica gel 13 may adsorb a part of PCBs so that the recovery rate of the PCBs may be lowered.

In the multilayer silica gel 13, the bulk density of the sulfuric acid silica gel in the upper layer 14 is usually set preferably into the range of 0.3 to 1.1 g/cm$^3$, more preferably into the range of 0.5 to 1.0 g/cm$^3$. The bulk density of the nitrate silica gel in the lower layer 15 is usually set preferably into the range of 0.3 to 1.0 g/cm$^3$, more preferably into the range of 0.4 to 0.9 g/cm$^3$. When the bulk densities of the upper layer 14 and the lower layer 15 are set in this manner, the developing rate of an aliphatic hydrocarbon solvent described later can be appropriately adjusted in the multilayer silica gel 13, and thus in an extracting operation described later, a high-purity PCBs solution less laced with an interfering substance can be obtained by use of the aliphatic hydrocarbon solvent in an appropriate amount.

The second column 20 is formed in a cylindrical shape having the same outside diameter and inside diameter as the lower end 10a of the first column 10, and the upper end and the lower end thereof have openings 21 and 22, respectively. This second column 20 is made of, for example, glass, or a plastic having chemical-resistance, solvent-resistance and heat-resistance. The inside of the second column is packed with a layer into which alumina is filled, that is, an alumina layer 23.

The alumina used in the alumina layer 23 is not particularly limited as long as it is capable of adsorbing PCBs, and may be any one of basic alumina, neutral alumina and acidic alumina. The alumina to be used may have various degrees of activity.

In the alumina layer 23, the bulk density of the alumina is not particularly limited, and is usually set preferably into the range of 0.5 to 1.2 g/cm$^3$, more preferably into the range of 0.8 to 1.1 g/cm$^3$. When the bulk density of the alumina is set in this manner, the developing rates of the aliphatic hydrocarbon solvent and of an extracting solvent, which will be described later, can be appropriately adjusted in the alumina layer 23, and thus in the extracting operation described later, a high-purity PCBs solution less laced with the interfering substance can be obtained by using the aliphatic hydrocarbon solvent and the extracting solvent in appropriate amounts, respectively.

The sulfuric acid silica gel, the nitrate silica gel and the alumina used in the column 1 can be stored after the preparation and used as needed. When they are stored, it is preferred, in order to suppress their deterioration, that they are put into sealed containers to block out water and ultraviolet rays.

The connecting member 30, which is a cylindrical member into which the lower end 10a of the first column 10 and the upper end of the second column 20 can be inserted, is formed of, for example, a plastic having heat-resistance as well as solvent-resistance against various solvents, in particular, hydrocarbon solvents. Through this connecting member 30, the lower end 10a of the first column 10 and the upper end of the second column 20 can be connected to each other so as to be attached to and detached from each other. Accordingly, in the column 1 composed of the first column 10 and the second column 20, the alumina layer 23 region is independently separable from the upper layer 14 and the lower layer 15.

In the column 1, the size of the first column 10 (the size of that portion of the column which can be packed with the upper layer 14 and the lower layer 15) is preferably from 10 to 20 mm in inside diameter and from 30 to 110 mm in length. The size of the second column 20 (the size of that portion of the column which can be packed with the alumina layer 23) is preferably from 2.0 to 10.0 mm in inside diameter and from 10 to 200 mm in length.

The following describes a process for extracting PCBs, using the column 1. Herein, a description is made about an example wherein for the analysis of the concentration of PCBs contained in an oily liquid, the PCBs are extracted from the oily liquid.

Figure 2:
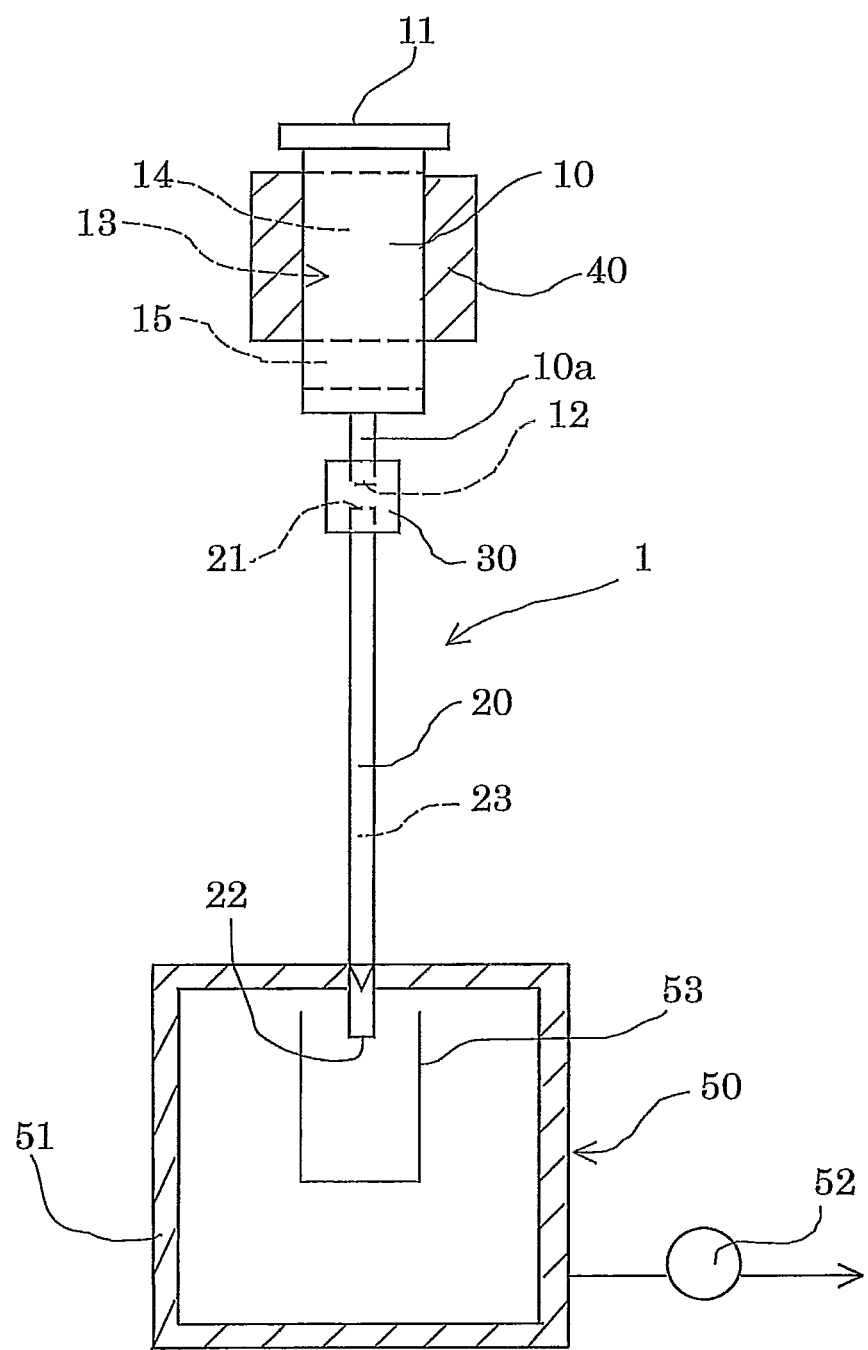
FIG. 2 is a diagram illustrating a step of an extracting operation using the above column.

As illustrated in FIG. 2, in this extracting process, first, a first heating device 40 is arranged around the upper layer 14 of the first column 10, and further a suction device 50 is fitted to the lower end of the second column 20. The first heating device 40 may be a heater, a Peltier device, or the like, and is used to heat the whole of the upper layer 14 to a required temperature. The suction device 50 has a container 51 capable of hermetically accommodating the lower end of the second column 20 and a pump 52 for reducing the pressure in the container 51. Inside the container 51, a solvent vessel 53 is arranged for receiving an aliphatic hydrocarbon solvent described later after passage through the column 1.

Next, from an oily liquid, a sample is collected in a small or trace amount (usually about 1.0 to 500 mg). This sample is added from the opening 11 in the upper end of the first column 10 to the upper layer 14. The added sample penetrates into the upper layer 14 of the first column 10 so as to be held therein. Then the first heating device 40 is activated thereby heating the upper layer 14 and keeping it heated for a predetermined time. In this way, interfering substances as described above, which are impurities contained in the sample and are substances other than PCBs, in particular, aromatic compounds, react with the sulfuric acid silica gel in the upper layer 14, so that most of the interfering substances decompose. The resulting decomposition products are adsorbed by the upper layer 14 so as to be held therein. Since the sulfuric acid silica gel exhibits a strong dehydrating action, the upper layer 14 effectively absorbs water incorporated in the sample.

In this step, the heating temperature of the upper layer 14 is set at least to 35° C., preferably to 50° C. or higher, more preferably 60° C. or higher. The upper limit of the heating temperature is not particularly limited. Usually, the limit is preferably 90° C. or lower from the viewpoint of safety. If the heating temperature is lower than 35° C., the reaction between the interfering substances contained in the sample and the sulfuric acid silica gel does not advance smoothly, so that the PCBs are not easily extracted from the sample in a short time. Usually, the period for heating the upper layer 14 is set preferably into the range of 10 to 60 minutes. If the heating period is less than 10 minutes, the interfering substances contained in the sample decompose insufficiently. Thus, the interfering substances may be incorporated in a finally-yielded extract of the PCBs.

When the oily liquid contains or may contain the interfering substances in a large amount, it is preferred to add the sample to the upper layer 14 of the first column 10 in this step and further add, to the upper layer 14, a hydrocarbon solvent capable of dissolving the sample, that is, the oily liquid. In this way, the sample is diluted with the hydrocarbon solvent so that the contacting efficiency between the sample and the sulfuric acid silica gel is improved to enhance the reaction efficiency therebetween. For this reason, in the upper layer 14, the interfering substances contained in the sample, in particular, the aromatic compounds are efficiently decomposed in a shorter time. As a result, the time required for the extraction of the PCBs can be shortened.

The hydrocarbon solvent usable herein is usually an aliphatic hydrocarbon solvent having 5 to 8 carbon atoms, examples thereof including n-pentane, n-hexane, n-heptane, n-octane, isooctane, and cyclohexane. It is necessary to select, as the hydrocarbon solvent, a solvent having a boiling point not lower than the heating temperature of the upper layer 14. If the boiling point of the hydrocarbon solvent does not satisfy this requirement, the hydrocarbon solvent volatilizes speedily when the first column 10 is heated. Thus, the above-mentioned reaction efficiency does not become high easily.

Usually, the hydrocarbon solvent may be added to the upper layer 14 of the first column 10 just after the sample is added thereto, or may be added to the sample in advance.

The upper layer 14 heated in the above process for the predetermined time is then cooled to ordinary temperature (usually room temperature of about 10 to 30° C.) by removing, or turning off the switch of, the first heating unit 40 and then leaving the layer 14.

Figure 3:
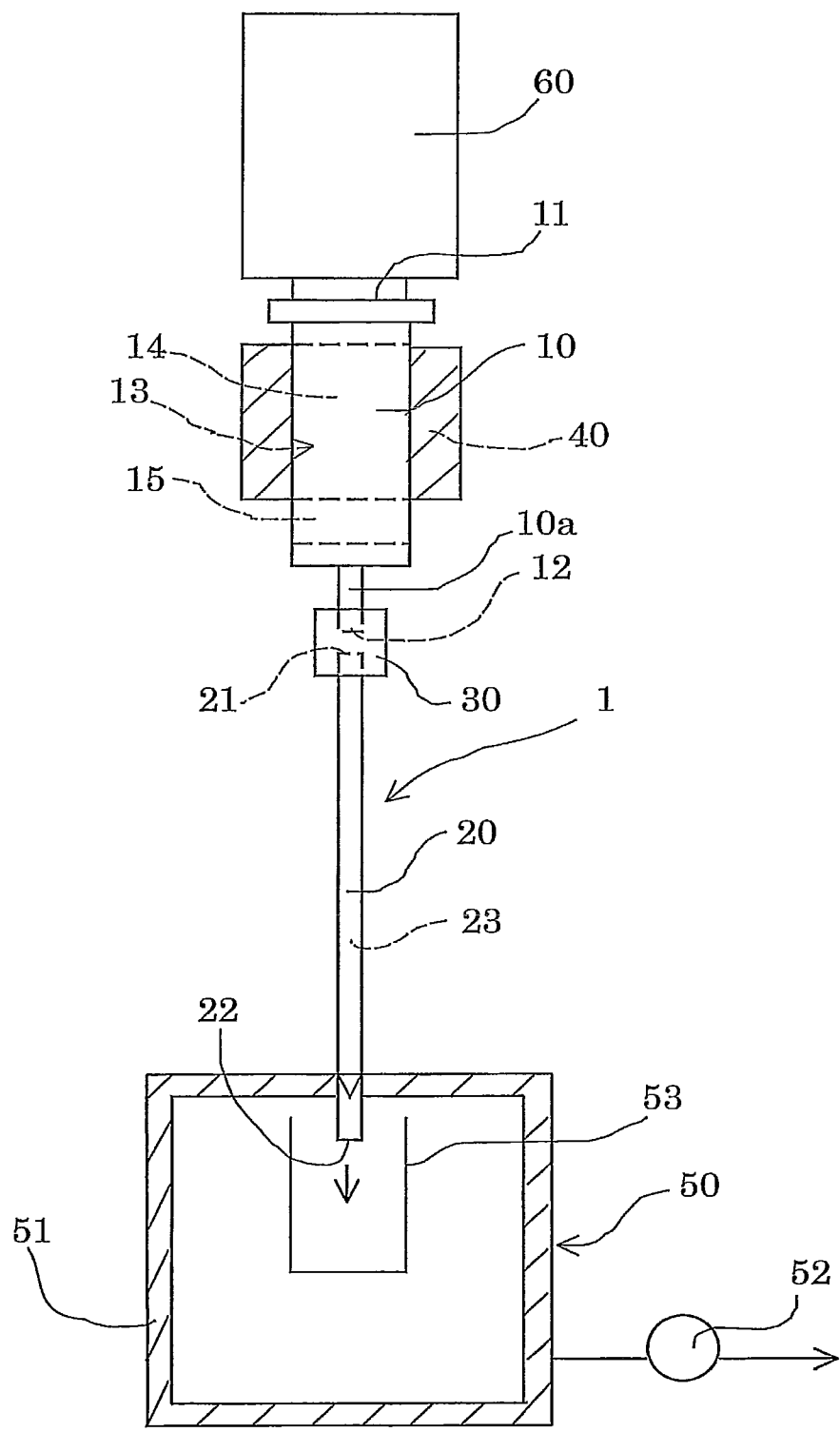
FIG. 3 is a diagram illustrating another step of the extracting operation using the above column.

Next, as illustrated in FIG. 3, a first reservoir 60 for supplying a solvent to the first column 10 is fitted into the opening 11, at the side of the upper end, of the first column 10, and an aliphatic hydrocarbon solvent is stored in the first reservoir 60. When the pump 52 is actuated, the pressure in the container 51 is reduced so that the aliphatic hydrocarbon solvent stored in the first reservoir 60 is supplied continuously and gradually to the first column 10. The aliphatic hydrocarbon solvent supplied from the first reservoir 60 into the first column 10 is supplied to the upper layer 14, then passed through the upper layer 14, supplied to the lower layer 15, and passed through the lower layer 15. The aliphatic hydrocarbon solvent passed through the lower layer 15 is then discharged from the opening 12 of the first column 10 through the connecting member 30 and flowed from the opening 21 into the second column 20.

At this time, the PCBs and the oily liquid retained in the upper layer 14 are dissolved in the aliphatic hydrocarbon solvent, and then passed, together with the aliphatic hydrocarbon solvent, through the lower layer 15 into the second column 20. On the other hand, the interfering substances that remain in the upper layer 14 and the decomposition products that are in a free state without being captured by the upper layer 14 are dissolved in the aliphatic hydrocarbon solvent, and then transferred into the lower layer 15. The interfering substances and the decomposition products transferred into the lower layer 15 are partially decomposed by the action of the nitrate silica gel, in particular, of nitrate ions dissociated from the nitrate silica gel, while a larger part of them is adsorbed onto the nitrate silica gel to be held therein. As a result, the interfering substances are separated from the PCBs.

The aliphatic hydrocarbon solvent flowed into the second column 20 is passed through the alumina layer 23, and discharged from the opening 22 to be received by the solvent vessel 53 in the container 51. At this time, the PCBs dissolved in the aliphatic hydrocarbon solvent from the first column 10 are captured by the alumina layer 23 and retained in the second column 20. PCBs are easily captured by the alumina layer 23 and thus retained mainly in the vicinity of the opening 21 in the upper end of the second column 20. On the other hand, the interfering substances remaining in the aliphatic hydrocarbon solvent from the first column 10, the decomposition products therefrom, and the oily liquid are passed through the alumina layer 23, together with the aliphatic hydrocarbon solvent, and then received by the solvent vessel 53.

The aliphatic hydrocarbon solvent used in this process is capable of dissolving the PCBs retained in the first column 10 and is usually an aliphatic saturated hydrocarbon solvent having 5 to 8 carbon atoms, for example n-pentane, n-hexane, n-heptane, n-octane, isooctane, and cyclohexane. Particularly, n-hexane is preferable. It is preferred that the amount of the aliphatic hydrocarbon solvent stored in the first reservoir 60, that is, the total amount of the aliphatic hydrocarbon solvent supplied into the first column 10 is usually set into the range of 10 to 120 mL. It is also preferred that the rate of feed of the aliphatic hydrocarbon solvent from the first reservoir 60 is usually set into the range of 0.2 to 5.0 mL/min. by regulating the depressurized state in the container 51 with the pump 52.

Figure 4:
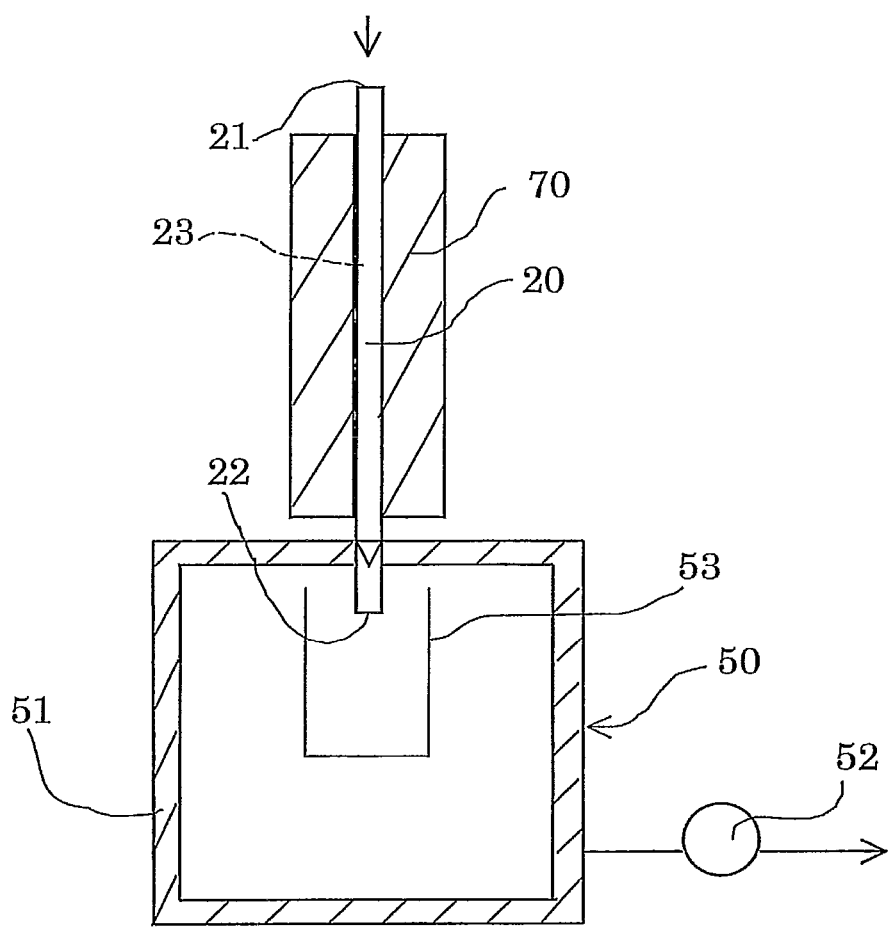
FIG. 4 is a diagram illustrating still another step of the extracting operation using the above column.

Next, the connecting member 30 is removed to separate the second column 20 and the first column 10 from each other. As illustrated in FIG. 4, a second heating device 70 is then arranged around the second column 20. The second heating device 70 used herein is similar to the first heating device 40. While the second column 20 is heated to the range of about 35 to 90° C. by means of the second heating device 70, the pump 52 is actuated to supply an inert gas such as nitrogen gas or air into the second column 20 through the opening 21 at the upper end. In this way, the solvent such as the aliphatic hydrocarbon solvent remaining in the second column 20 is discharged, together with the inert gas, from the opening 22 at the lower end of the second column 20, so that the solvent such as the aliphatic hydrocarbon solvent are removed from the alumina layer 23. As a result, the alumina layer 23 in the second column 20 is dried.

Figure 5:
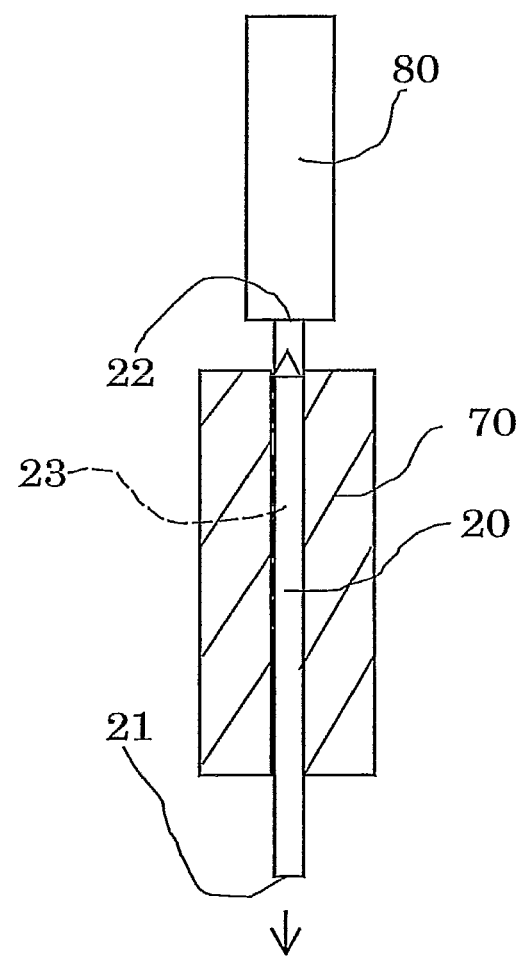
FIG. 5 is a diagram illustrating a further step of the extracting operation using the above column.

Then, the second column 20 is removed from the suction device 50 and turned upside down by inverting it together with the second heating device 70. As illustrated in FIG. 5, a second reservoir 80 for supplying a solvent is then fitted into the opening 22 of the second column 20 thus turned up by inversion. A predetermined amount of an extracting solvent is supplied into the second reservoir 80.

The extracting solvent supplied into the second reservoir 80 flows naturally by its own weight from the second reservoir 80 into the second column 20, so as to be supplied into the alumina layer 23. The extracting solvent then passes through the alumina layer 23 to be discharged from the opening 21 of the second column 20 thus turned down by inversion. At this time, the extracting solvent from the second reservoir 80 dissolves the PCBs captured by the alumina layer 23, so as to be discharged together with the PCBs from the opening 21. Accordingly, when the extracting solvent discharged from the opening 21 is secured, a solution of the PCBs, that is, the objective extract of the PCBs, is obtained. Since the PCBs are captured mainly in the vicinity of the opening 21 side of the alumina layer 23, substantially the total amount of the PCBs captured by the alumina layer 23 comes to be dissolved in the extracting solvent mainly in a first elute discharged from the second column 20. Accordingly, only by securing the first elute of the extracting solvent discharged from the opening 21, the objective extract of the PCBs can be obtained. This extract consists of the first elute of low volume and is thus in such a small volume as to be easily utilizable in an analytical operation described later.

In the extraction process, it is preferred to supply the extracting solvent into the second column 20 while the column 20 is heated by means of the second heating device 70. The heating temperature of the second column 20 is usually set so as to adjust the temperature of the alumina layer 23 preferably to at least 35° C., more preferably to 60° C. or higher, in particular, about 80° C. The upper limit of the heating temperature is usually about 90° C. from the viewpoint of safety. When the second column 20 is heated in this manner, the whole amount of the PCBs captured by the alumina layer 23 can be easily extracted with a smaller amount of the extracting solvent. Thus, the amount of the extract of the PCBs can be set smaller to be further utilizable in the analytical operation described later.

The extracting solvent used in this extracting step may be selected in accordance with an analyzing method described later. In other words, when gas chromatographic method is used as the analyzing method, a solvent suitable therefor is used. Examples thereof include toluene, a mixed solvent of toluene and an aliphatic hydrocarbon solvent (for example, n-pentane, n-hexane, n-heptane, n-octane, isooctane, cyclohexane and the like), and a mixed solvent of an organochlorine solvent (for example, dichloromethane, trichloromethane, tetrachloromethane and the like), and an aliphatic hydrocarbon solvent (for example, n-pentane, n-hexane, n-heptane, n-octane, isooctane, cyclohexane and the like). Among these solvents, toluene is preferable because by using it in a smaller amount, the PCBs can be extracted from the alumina layer 23.

When bioassay is used as the analytical method, a solvent suitable therefor is used. Examples thereof include hydrophilic solvents such as dimethylsulfoxide (DMSO) and methanol.

The extract of the PCBs obtained by the above-described extracting process is a liquid from which the interfering substances have been removed by the treatment with the column 1, and is also a liquid obtained by removing the aliphatic hydrocarbon solvent from the alumina layer 23 and then supplying the extracting solvent into the second column 20. Thus, the extract can be high purity.

According to the extracting process of the present embodiment, the above-mentioned extract can be ordinarily obtained in a short time, which is from about 2 to 10 hours after the work-starting step (the step of adding the sample into the first column 10).

When the PCBs contained in the oily liquid are analyzed, the extract obtained in the extracting operation, that is, the solution of the PCBs in the extracting solvent is used as an analytical sample for gas chromatographic method or bioassay technique.

The gas chromatographic method can be carried out with gas chromatographic units equipped with various detectors. Usually, gas chromatography-mass spectrometry (GC-MS method) or a gas chromatography-electron capture detection (GC-ECD method), which is high in sensitive to PCBs, is preferably used. When GC-MS method is used, various techniques may be adopted, examples thereof including a GC-QMS technique and a GC-MS/MS technique.

According to the GC-MS method, the PCBs contained in the analytical sample can be quantitatively determined with respect to each isomer or each homologue, and thus a larger number of findings can be gained from the analysis results. Therefore, the GC-MS method is significant for the analysis of PCBs.

The bioassay technique may be, for example, an Ah receptor binding assay technique or an immunoassay technique using an anti-PCBs antibody.

The extract obtained in the above-described extracting operation may be used after being concentrated for analysis when needed.

Figure 6:
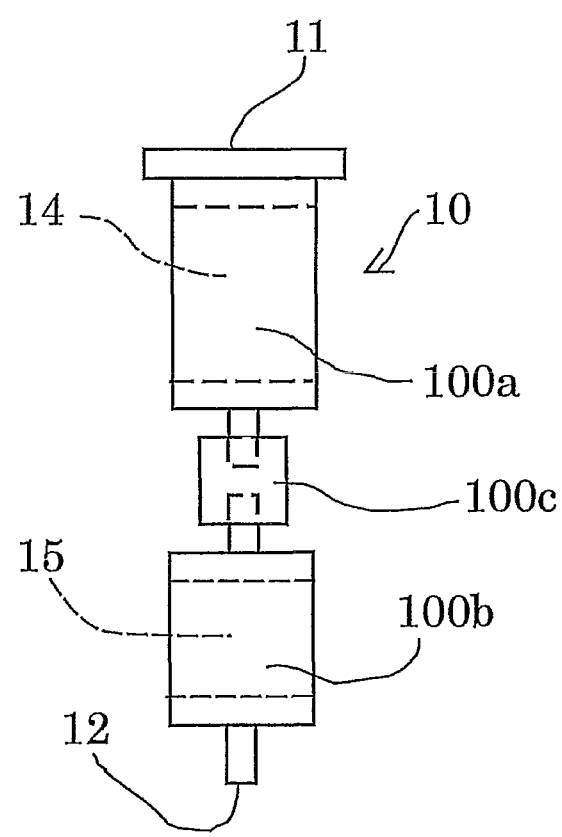
FIG. 6 is a partial schematic diagram of another example of the column usable in the process for extracting PCBs according to the present invention.

The above-mentioned embodiment may be modified, for example, as follows:

(1) In the above-mentioned embodiment, in the column 1, the first column 10 is composed of a single column packed with the multilayer silica gel 13 in which the upper layer 14 made of sulfuric acid silica gel is stacked on the lower layer 15 made of nitrate silica gel. Alternatively, as illustrated in FIG. 6, the first column 10 may be divided into a forward column 100a and a backward column 100b arranged vertically, which are connected detachably to each other through a connecting member 100c similar to the connecting member 30 described above. In the first column 10 in this case, the forward column 100a is packed with a sulfuric acid silica gel to form an upper layer 14 and the backward column 100b is packed with a nitrate silica gel to form a lower layer 15. When the first column 10 thus constituted is used to extract PCBs from an oily liquid, the forward column 100a only is heated by means of the first heating device 40.

(2) In the first column 10 or the like, used in the embodiments described above, in which the upper layer 14 and the lower layer 15 have been stacked may be provided between the upper layer 14 and the lower layer 15 with a layer made of a usual silica gel, a glass stable to PCBs and aliphatic hydrocarbon solvents or a cotton matter or fibrous matter made of plastic or the like having solvent-resistance and heat-resistance. This layer may be arranged above the upper layer 14 or below the lower layer 15.

(3) In the embodiments described above, the columns such as the first column 10 and the second column 20 are connected to each other detachably through the connecting member 30 or the connecting member 100c but may be connected to each other with another means. For example, the columns may be provided in connecting portions with fitting parts with which the columns can be connected detachably to each other.

(4) In the embodiments described above, the suction device 50 is arranged in the lower end of the second column 20, and the aliphatic hydrocarbon solvent stored in the first reservoir 60 is supplied into the first column 10 by suction with the suction device 50. Alternatively, the aliphatic hydrocarbon solvent in the first reservoir 60 may drop naturally into the first column 10 without using the suction device 50. The aliphatic hydrocarbon solvent can also be supplied into the first column 10 with a metering pump such as a syringe pump or with a pressure device. Furthermore, the aliphatic hydrocarbon solvent may be supplied into the first column 10 by hand with a supplying tool such as a pipette.

(5) In the embodiments described above, the extracting solvent supplied into the second reservoir 80 is supplied naturally by its own weight into the second column 20. Alternatively, the extracting solvent can be supplied into the second column 20 with a metering pump such as a syringe pump or with a pressure device.

(6) In the embodiments described above, the extracting method of the present invention has been described by referring mainly to those cases wherein PCBs are extracted from a sample collected from an oily liquid such as an electric insulating oil in order to analyze the concentration of PCBs contained in the oily liquid. However, the present invention can be used for other purposes. For example, an oily liquid containing PCBs should be disposed of after detoxification of PCBs by decomposition, but when a large amount of the oily liquid should be disposed of, detoxification treatment may be hardly smoothly advanced. Hence, when the extracting process of the present invention is applied to an electric insulating oil to be disposed of, PCBs contained in the oily liquid can be converted into a small amount of a solution in an extracting solvent, thus facilitating the detoxification treatment of the PCBs.

In this case, since a larger amount of oily liquid as compared with the case of preparing an analytical sample of PCBs tend to be processed, the column 1 may be adjusted to a larger size corresponding to the amount of the oily liquid to be processed.

Hereinafter, the present invention will be described in more detail by way of experimental examples.

In the following experimental examples, electric insulating oils A, B, C and D described below were used as an oily liquid. Electric insulating oils used to prepare electric insulating oils A, B, C and D were confirmed to be free of PCBs by analysis of the GC-MS method (HRGC-HRMS method) specified in the official method.

(Electric Insulating Oil A)

An electric insulating oil removed from a junk transformer.

(Electric Insulating Oil B)

An electric insulating oil removed from a junk capacitor.

(Electric Insulating Oil C)

An electric insulating oil removed from a junk capacitor different in kind from the junk capacitor from which the electric insulating oil B was removed.

(Electric Insulating Oil D)

An electric, insulating oil prepared by adding a PCBs standard product (trade name: "KC-MIX", manufactured by GL Sciences Inc.) to a commercially available electric insulating oil (product manufactured by Matsumura Oil Co., Ltd. and adapted to the Japanese Industrial Standard, class 1, No. 2) so as to set the total concentration of PCBs in 1.0 mg/kg.

In the experimental examples described below, a separation column of the above-described embodiment illustrated in FIG. 1, in which the first and second columns specified as below are used, was used.

(First Column)

A column prepared by charging 1.0 g of a nitrate silica gel into a column having an inside diameter of 12 mm and a length of 60 mm to give a height of 13 mm, and then charging 3.5 g of sulfuric acid silica gel thereinto so as to give a height of 47 mm on the nitrate silica gel.

The nitrate silica gel used herein was prepared in the following manner. To 50 g of an activated silica gel (manufactured by Kanto Chemical Co., Inc.), the whole of a mixed aqueous solution prepared by dissolving 13 g (in terms of copper nitrate) of copper nitrate trihydrate (manufactured by Wako Pure Chemical Industries, Ltd.) and 18 g of silver nitrate (manufactured by Wako Pure Chemical Industries, Ltd.) in 70 mL of distilled water was added and mixed uniformly. Then thus treated silica gel was dried at 80° C. under reduced pressure, with the use of rotary evaporator. In the resultant nitrate silica gel, the ratio by mole of the copper element (Cu) to the silver element (Ag), Cu:Ag, was 1:1.5.

The sulfuric acid silica gel was prepared by adding 44 g of concentrated sulfuric acid (manufactured by Wako Pure Chemical Industries, Ltd.) uniformly to 56 g of an activated silica gel (manufactured by Kanto Chemical Co., Inc.), and then drying the activated silica gel.

(Second Column)

A column obtained by charging 0.5 g of alumina (manufactured by MP Biomedicals) into a column having an inside diameter of 3 mm and a length of 70 mm to give a height of 70 mm.

Experimental Example 1

To the upper end side of the first column (the nitrate silica gel used in this column was aged one hour after the preparation), 100 mg of the electric insulating oil A and 2 mL of isooctane were added. The sulfuric acid silica gel layer in the first column was heated at 80° C. for 30 minutes and then cooled to room temperature. Thereafter, the second column was connected to the lower end side of the first column. At a rate of 1 mL/min., 20 mL of n-hexane was supplied to the upper end of the first column and then discharged from the lower end of the second column. After supply of n-hexane, the first and second columns were separated from each other, and then n-hexane remaining in the second column was removed. At this time, nitrogen gas was supplied to the second column while the second column was heated to 80° C.

Next, toluene was supplied into the second column, reversely to the direction in which n-hexane was passed, at room temperature (20° C.), and a toluene solution passed through the second column was collected. At this time, the supply rate of toluene was set at 50 μL/min., and 340 μL of an initial elute discharged from the second column was collected. The elapsed time from the start of the operation to the gain of the toluene solution of the initial elute was about 2.2 hours.

The collected toluene solution was analyzed by a GC-MS method (HRGC-HRMS method) in accordance with the official method.

Figure 7:
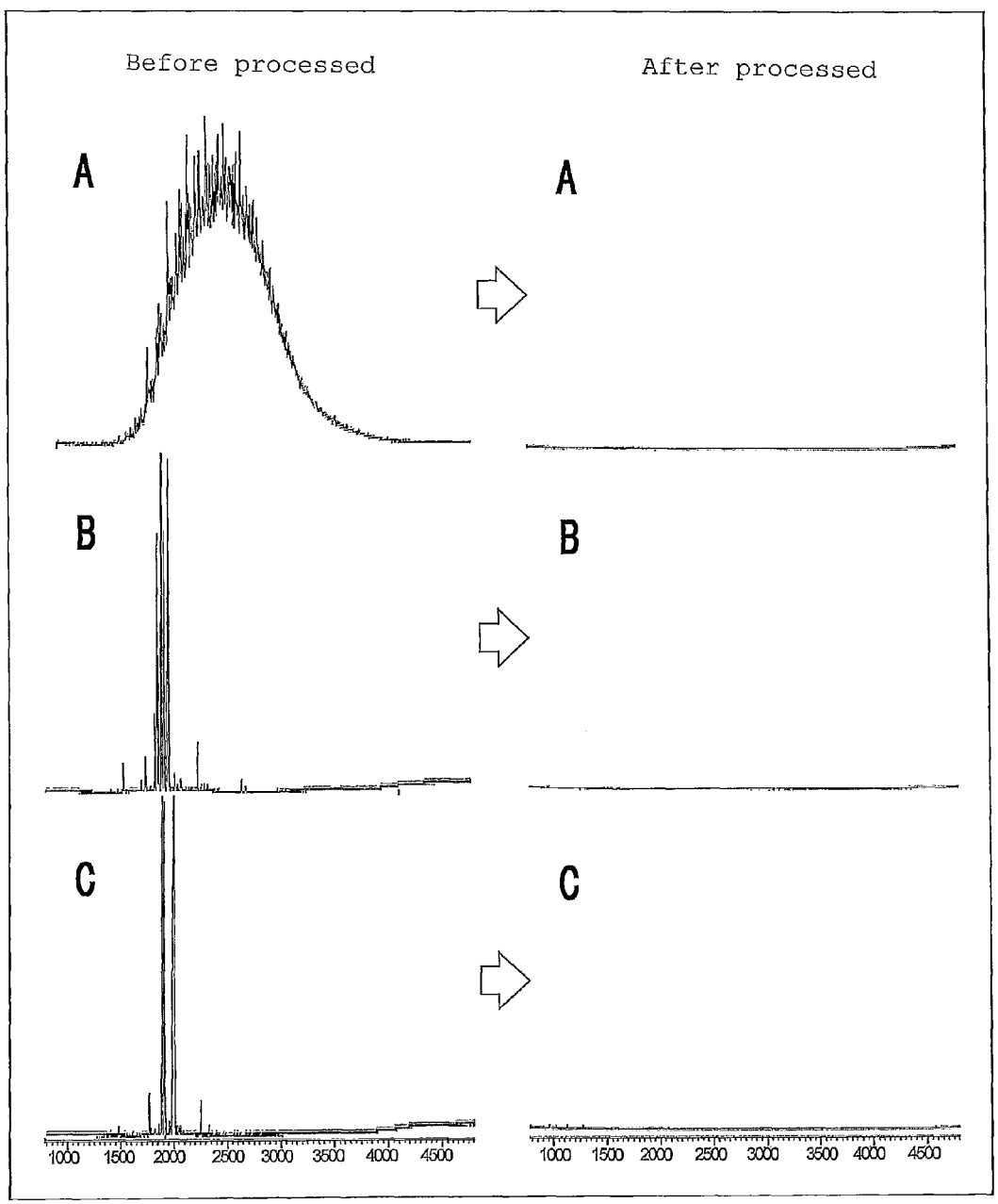
FIG. 7 is a chromatogram showing analysis results of electric insulating oils A, B and C before and after the oils are treated in Experimental Example 1, the results being obtained according to a GC-MS technique.

Toluene solutions obtained from the electric insulating oils B and C respectively by the same process were also analyzed by a GC-MS method (HRGC-HRMS method) in accordance with the official method. The results are shown in FIG. 7. In FIG. 7 are together shown results obtained by analyzing the electric insulating oils A, B and C before the above-mentioned process by the GC-MS method (HRGC-HRMS method) in accordance with the official method.

According to FIG. 7, it is demonstrated by the analysis results before the process that the electric insulating oils A, B and C contain many components. However, it is understood that after the process, these components are highly removed from the oils.

Experimental Example 2

Figure 8:
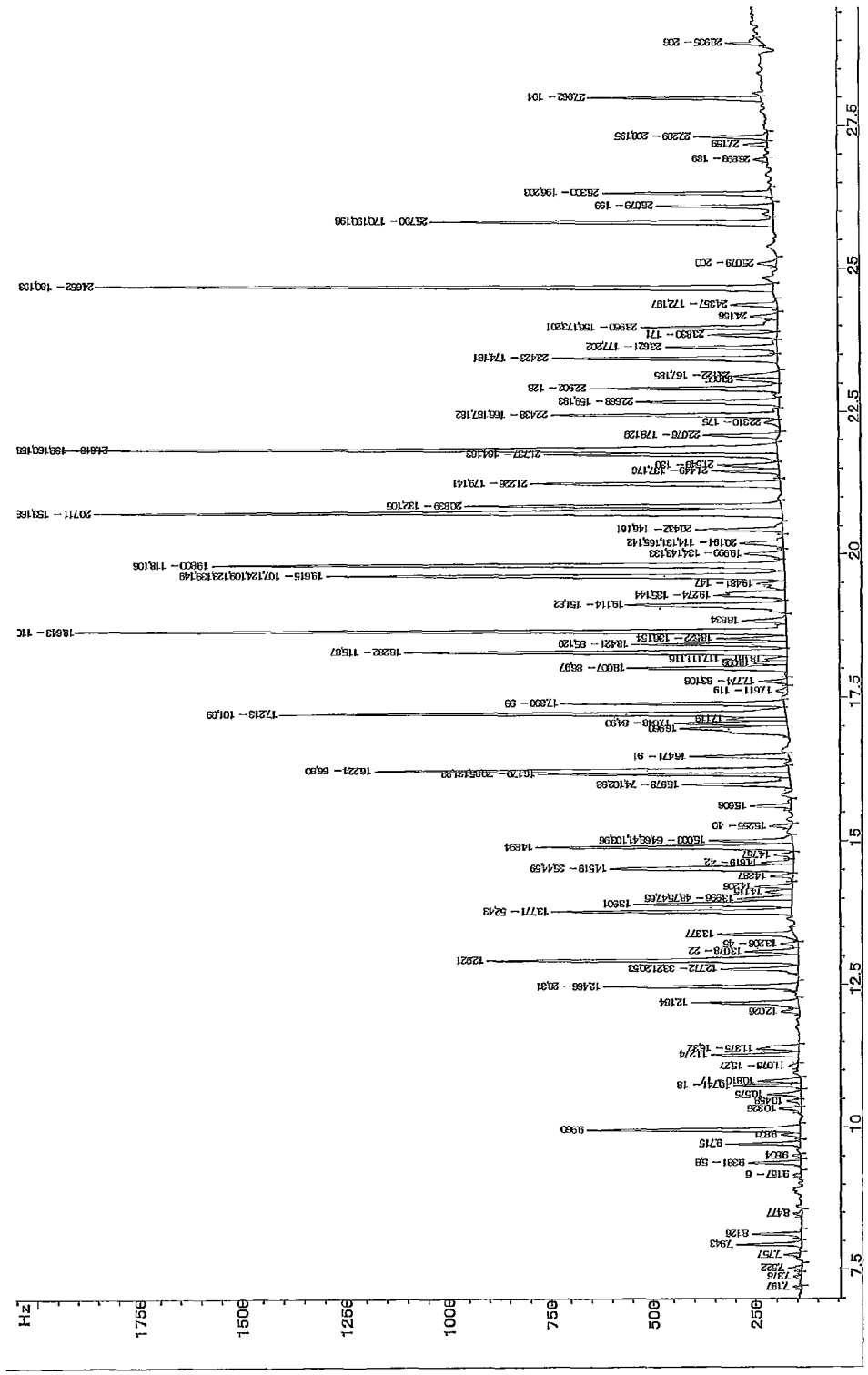
FIG. 8 is a chromatogram showing analysis results according to a GC-ECD technique in Experimental Example 2.
Figure 9:
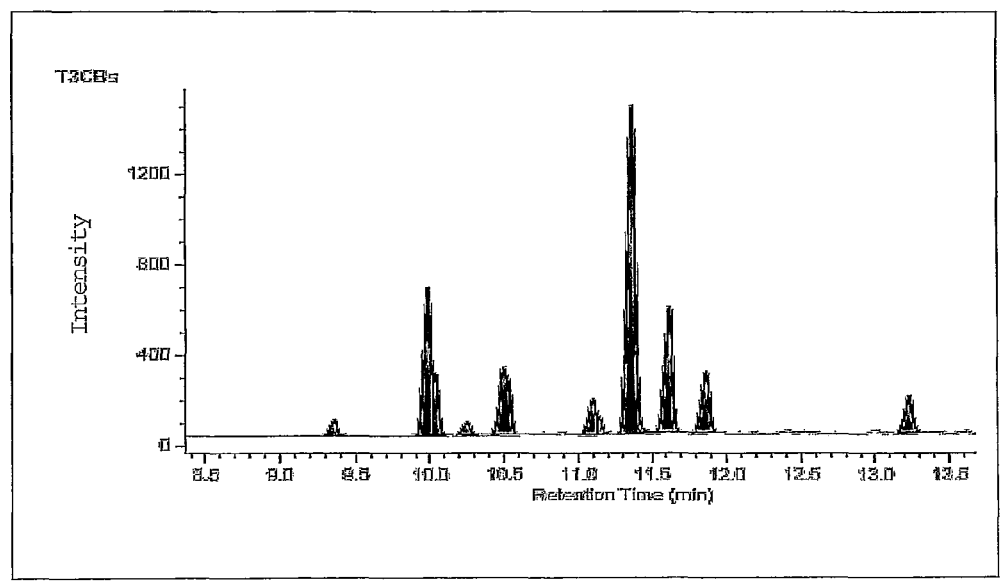
FIG. 9 is a part of a chromatogram showing analysis results according to a GC-QMS technique in Experimental Example 2.
Figure 10:
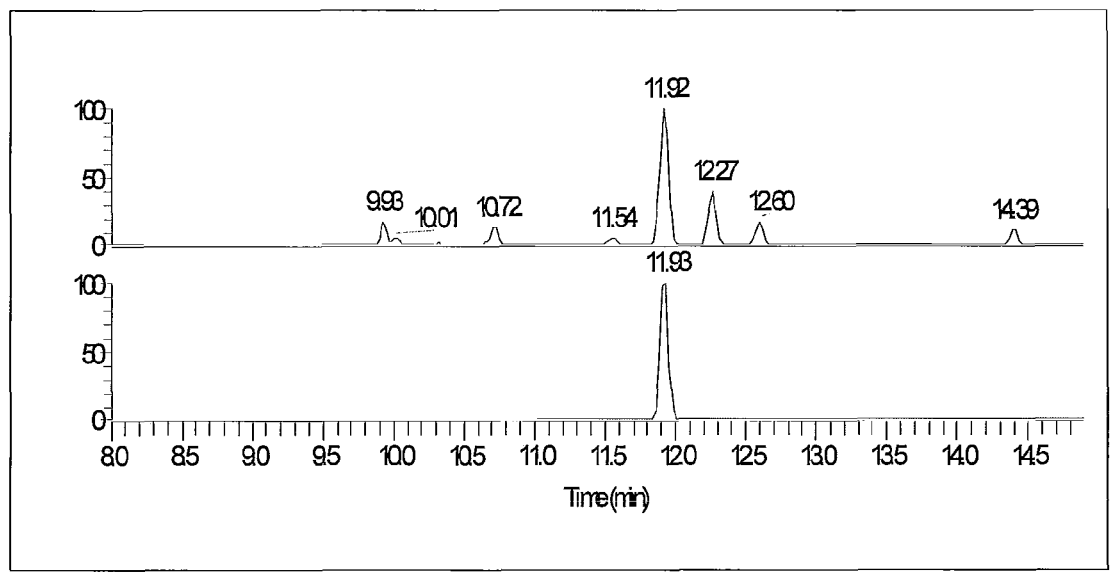
FIG. 10 is a part of a chromatogram showing analysis results according to a GC-MS/MS technique in Experimental Example 2.

The electric insulating oil D was processed by the same manner as in Experimental Example 1 to obtain an extract of PCBs. This extract was analyzed by three different gas chromatographic methods, namely a GC-ECD method, a GC-QMS method, and a GC-MS/MS method. The results are shown in FIG. 8 to FIG. 10. FIG. 8 (chromatogram resulting from the GC-ECD method) shows the analysis results of all the PCBs. On the other hand, FIG. 9 (chromatogram resulting from the GC-QMS method) and FIG. 10 (chromatogram resulting from the GC-MS/MS method) show data regarding trichloro PCBs only, in order to avoid a complicated representation.

According to FIG. 8 to FIG. 10, with respect to any of the results, a base line is substantially flat and stable, and also peak forms of the PCBs are good. Accordingly, it is understood that when an extract of PCBs is obtained from the electric insulating oil D by the process of Experimental Example 1, interfering substances contained in the electric insulating oil D, such as aromatic compounds and paraffins, can be sufficiently removed so that the PCBs contained in the electric insulating oil D can be quantitatively determined with high accuracy.

Experimental Example 3

According to an extracting process described in Example 15 of the pamphlet of International Publication WO 2008/123393 (hereinafter, the process will be referred to as the comparative extracting process), an extract of PCBs was obtained from the electric insulating oil D. The comparative extracting process is a process uses, in place of the first column used in Experimental Example 1, a column in which a sulfuric acid silica gel, a copper nitrate silica gel and a silver nitrate silica gel are stacked in this order from the top to the bottom in three layers. This column corresponds to the first column used in Experimental Example 1 wherein instead of the nitrate silica gel, a copper nitrate silica gel and a silver nitrate silica gel are stacked. The copper nitrate silica gel and the silver nitrate silica gel used in this experiment were aged one hour after the preparation.

Figure 11:
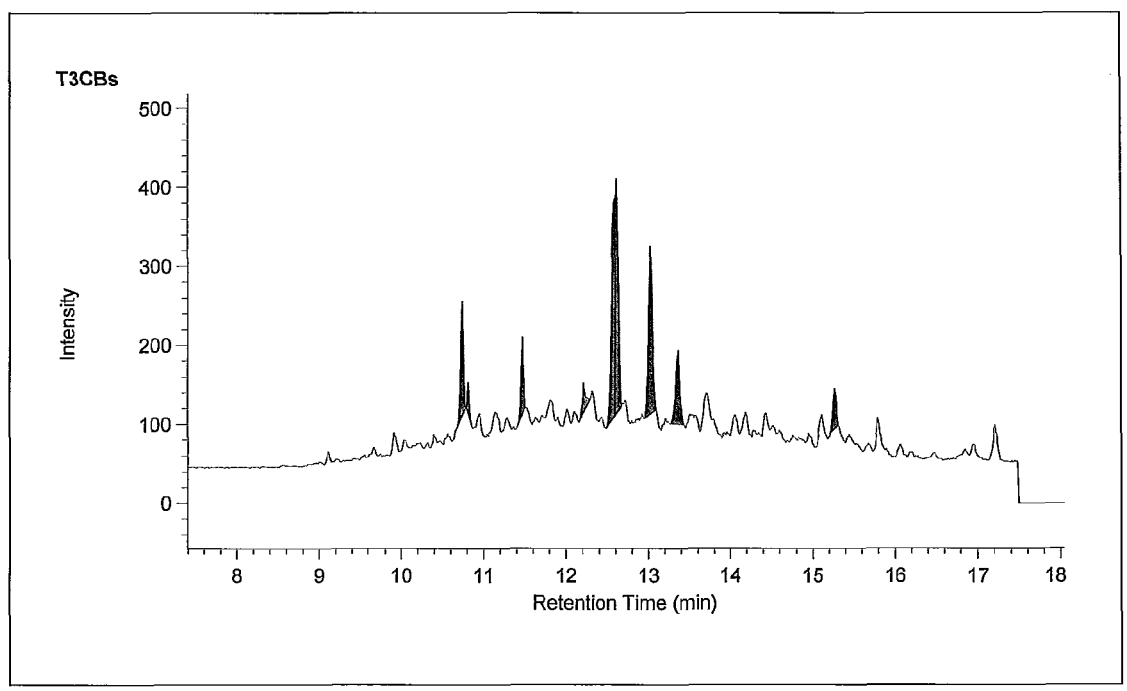
FIG. 11 is a part of a chromatogram in the case of using a GC-QMS technique to analyze an extract solution of PCBs yielded by a comparative extraction method of Experimental Example 3.

FIG. 11 shows the results obtained by analyzing according to a GC-QMS method the PCBs extract obtained by the comparative extracting process. In FIG. 11, partial data with respect to trichloro PCBs only are shown in order to compare the data with those in FIG. 9.

When FIG. 9 is compared with FIG. 11, the base line in FIG. 9 is stable but that in FIG. 11 is instable. This results demonstrate that when a sample for analyzing PCBs, that is, an extract of PCBs is prepared from the electric insulating oil D, the PCBs contained in the electric insulating oil D can be highly separated from interfering substances therein according to the process of Experimental Example 1 while the separation is not sufficiently attained according to the comparative extracting process.

Experimental Example 4

In the same way as in Experimental Example 1, a nitrate silica gel aged 7 months after the preparation was used to obtain an extract of PCBs from the electric insulating oil D, and then the PCBs contained in this extract were analyzed according to a GC-QMS method. Moreover, in the same way as in Experimental Example 3, a copper nitrate silica gel and a silver nitrate silica gel, both of which were aged 3 months after the preparation, were used to obtain an extract of PCBs from the electric insulating oil D, and then the PCBs contained in this extract were analyzed according to a GC-QMS method.

Figure 12:
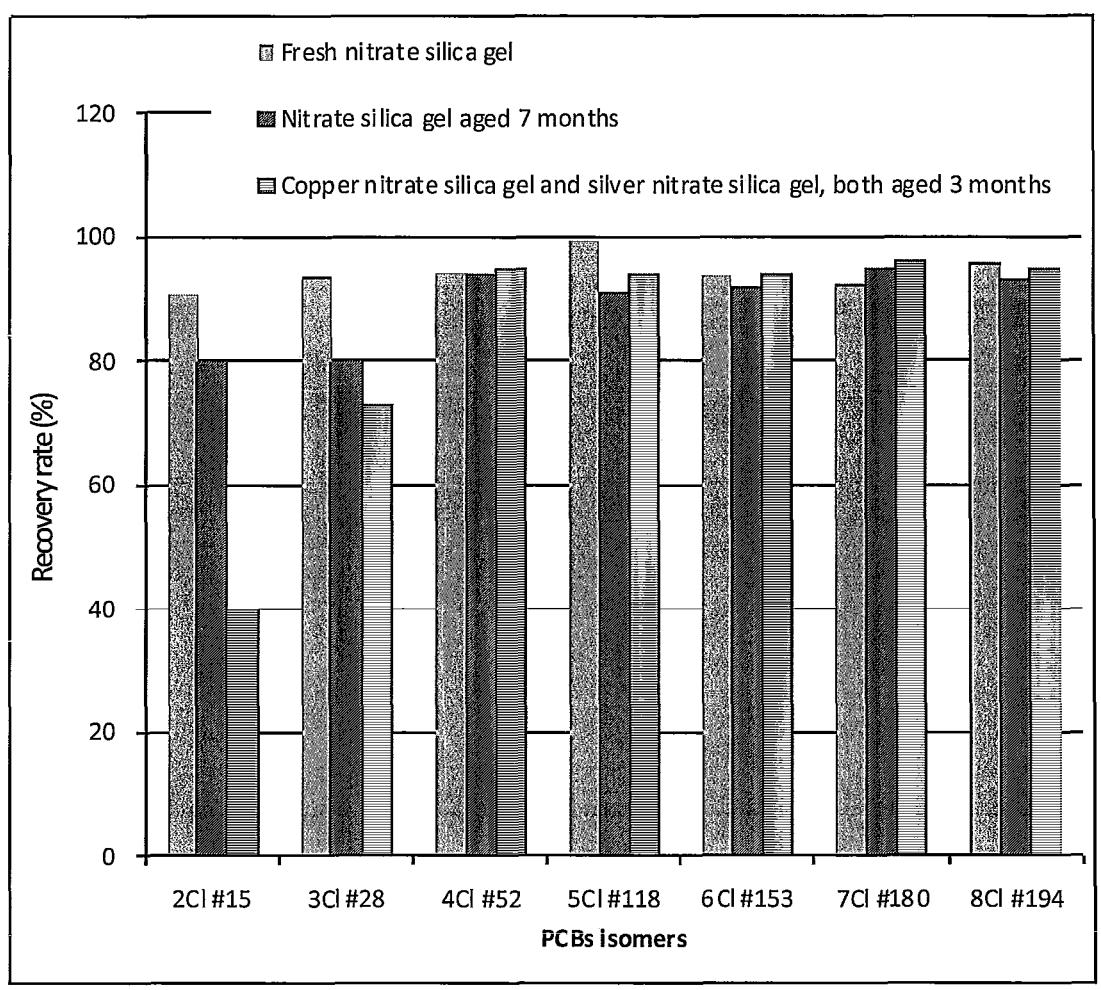
FIG. 12 is a graph showing results of Experimental Example 4.

FIG. 12 shows the recovery rates, which are obtained from the analysis results of the GC-QMS method, of individual isomers of dichloro PCBs, trichloro PCBs, tetrachloro PCBs, pentachloro PCBs, hexachloro PCBs, heptachloro PCBs and octachloro PCBs (the extraction rates of individual isomers of these PCBs contained in the electric insulating oil D). In FIG. 12, the data "fresh nitrate silica gel" are those read out from the analysis results of the GC-QMS method in Experimental Example 2.

According to FIG. 12, in the case of using the copper nitrate silica gel and the silver nitrate silica gel, both of which were aged 3 months after the preparation, the recovery rates of low chlorine number PCBs, in particular dichloro PCBs, are very low. Contrarily, in the case of using the nitrate silica gel aged 7 months after the preparation, the recovery rates of any chlorine number PCBs are kept at 80% or more. These result demonstrates for a column using a nitrate silica gel that its function of extracting PCBs from an electric insulating oil is less deteriorated even when the column is stored over a long term before use, as compared with a column in which a copper nitrate silica gel and a silver nitrate silica gel are stacked.

Experimental Example 5

Samples for analyzing PCBs were prepared by the official method from 20 different PCBs-containing electric insulating oils which were removed from used transformers or capacitors in the past and then stored for a long term, and then analyzed by the GC-MS method (HRGC-HRMS method) specified in the official method. On the other hand, samples for analyzing PCBs were prepared by the method of Experimental Example 1 from the same 20 different PCBs-containing electric insulating oils, and then analyzed by three different gas chromatographic method, namely a GC-ECD method, a GC-QMS method and a GC-MS/MS method.

Figure 13:
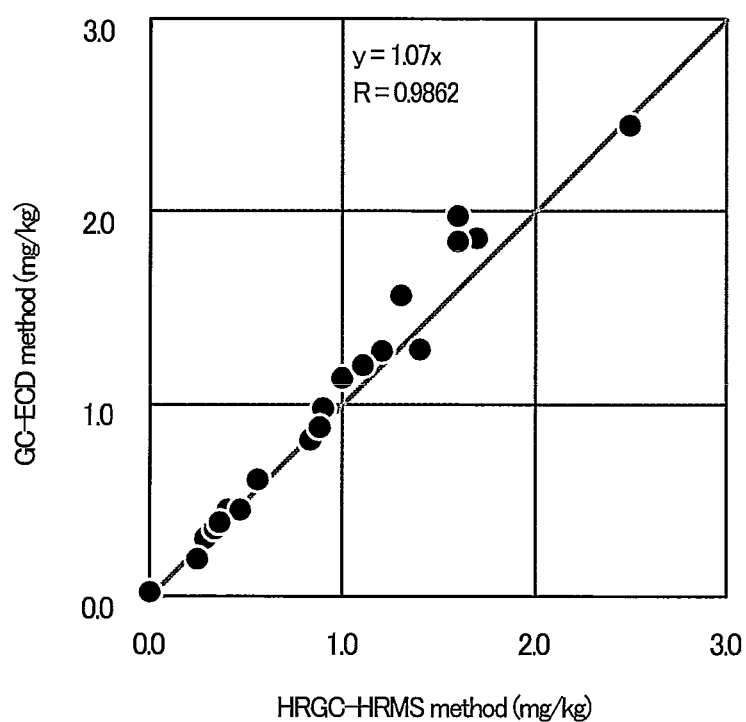
FIG. 13 is a chart of Experimental Example 5, showing a correlative relationship between results in the case of preparing and analyzing samples by the official method, and results in the case of preparing samples according to Experimental Example 1 and then analyzing the samples by a GC-ECD technique.
Figure 14:
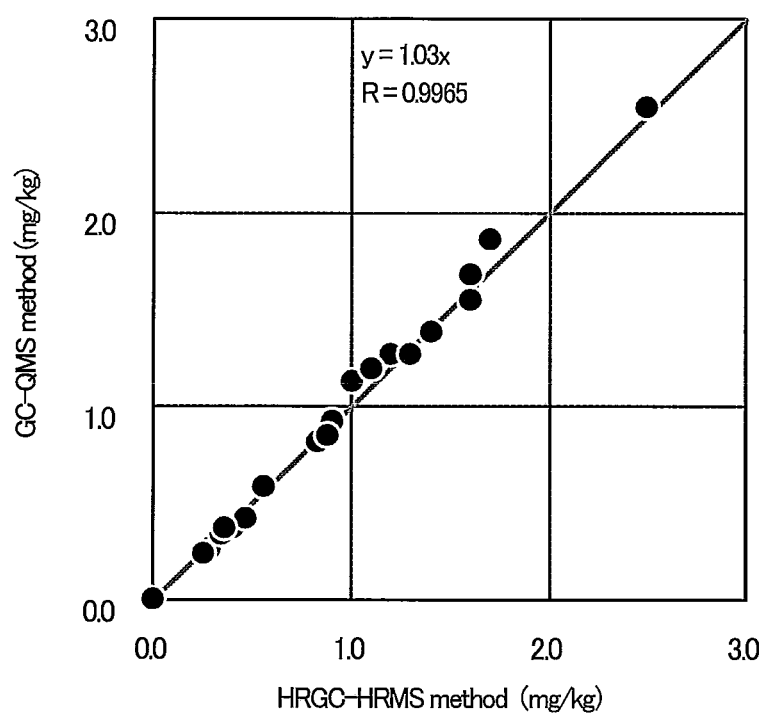
FIG. 14 is a chart of Experimental Example 5, showing a correlative relationship between the results in the case of preparing and analyzing samples by the official method, and results in the case of preparing samples according to Experimental Example 1 and then analyzing the samples by a GC-QMS technique.
Figure 15:
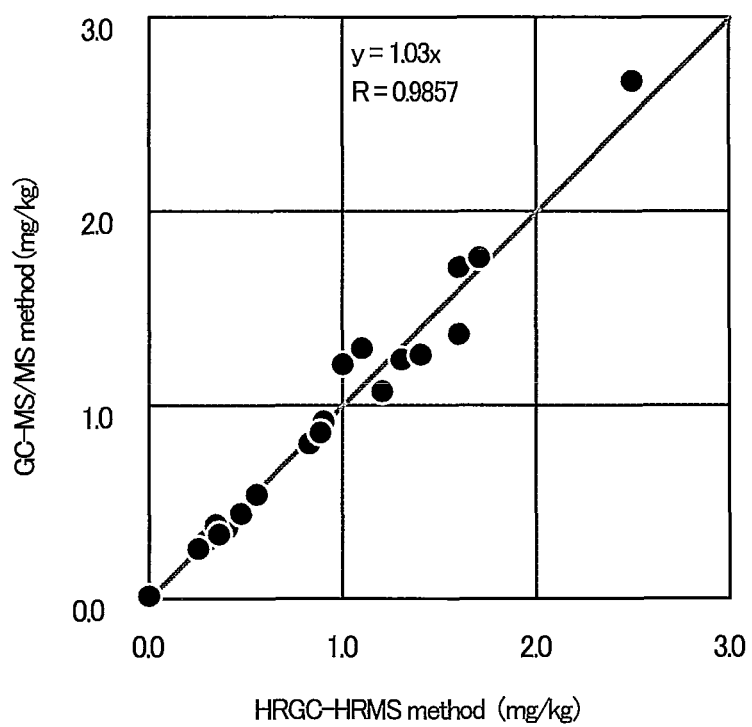
FIG. 15 is a chart of Experimental Example 5, showing a correlative relationship between the results in the case of preparing and analyzing samples by the official method, and results in the case of preparing the analyzing samples according to Experimental Example 1 and then analyzing the samples by a GC-MS/MS technique.

Each of FIGS. 13 to 15 shows a correlative relationship between the results in the case of preparing the analyzing samples by the official method and the results in the case of preparing the analyzing samples by the method of Experimental Example 1. In each of the figures, the transverse axis represents the results in the case of preparing the analyzing samples by the official method, and the vertical axis represents the results in the case of preparing the analyzing samples by the method of Experimental Example 1. In each of the correlative relationships, the correlation coefficient R was as high as 0.98 or more. It is therefore understood that the method for preparing an analyzing sample according to the method of Experimental Example 1 is suitable as an alternative to the official method.

The present invention can be carried out in various other forms without departure from the spirit and major features of the present invention. Accordingly, the embodiments and examples described above are merely illustrative in all aspects and are not to be construed as restrictive. The scope of the present invention is defined by the claims and is not restricted in any sense by the description of the specification. Any variations and modifications that fall within equivalence of the claims are intended to fall within the scope of the present invention.

The invention claimed is:

1. A purifying agent for an oily liquid containing polychlorinated biphenyls, which is for removing, from the oily liquid, a substance which may interfere with an analysis of polychlorinated biphenyls contained in the oily liquid, said purifying agent comprising:
   a nitrate silica gel yielded by adding a mixed aqueous solution of copper nitrate and silver nitrate to an activated silica gel uniformly and subsequently drying the activated silica gel, wherein a ratio between the copper nitrate and the silver nitrate in the aqueous solution is adjusted to set the ratio by mole of the copper element to the silver element in the nitrate silica gel (the copper element:the silver element) into the range 1:0.5 to 1:2.0.

2. The purifying agent of claim 1, wherein the activated silica gel is dried under reduced pressure at a temperature of 80° C.

3. A purifying column for an oily liquid containing polychlorinated biphenyls, which is for removing, from the oily liquid, a substance which may interfere with an analysis of polychlorinated biphenyls contained in the oily liquid, said purifying column comprising:
   a first layer of a sulfuric acid silica gel, and
   a second layer of a purifying agent according to claim 1, arranged below the first layer.

4. The purifying column for an oily liquid containing polychlorinated biphenyls according to claim 3, wherein the first layer and the second layer are packed in the same column.

5. The purifying column for an oily liquid containing polychlorinated biphenyls according to claim 3, which comprises a forward column packed with the first layer, and a backward column packed with the second layer, the forward column and the backward column being connected to each other so as to be separable from each other.

6. A column for separating polychlorinated biphenyls from an oily liquid containing the polychlorinated biphenyls in order to analyze the polychlorinated biphenyls, said column comprising:
- a first column comprising a first layer of a sulfuric acid silica gel, and a second layer of a purifying agent according to claim 1, arranged below the first layer, and
- a second column packed with alumina and attachable to and detachable from the second layer side of the first column.

7. The column for separating polychlorinated biphenyls according to claim 6, wherein the first column is a single column with which the first layer and the second layer are packed.

8. The column for separating polychlorinated biphenyls according to claim 6, wherein the first column comprises a forward column with which the first layer is packed, and a backward column with which the second layer is packed, the forward column and the backward column being connected to each other so as to be separable from each other.

9. A method for extracting polychlorinated biphenyls from an oily liquid containing the polychlorinated biphenyls, comprising the steps of:
- adding the oily liquid to a sulfuric acid silica gel layer,
- allowing the sulfuric acid silica gel layer to which the oily liquid is added to be kept in a state heated to at least 35° C. for a predetermined period and then cooling the layer to ordinary temperature,
- supplying an aliphatic hydrocarbon solvent to the sulfuric acid silica gel layer cooled to ordinary temperature,
- allowing the aliphatic hydrocarbon solvent passed through the sulfuric acid silica gel layer to be supplied to, and passed through, a layer of a purifying agent according to claim 1,
- allowing the aliphatic hydrocarbon solvent passed through the purifying agent layer to be supplied to, and passed through, an alumina layer,
- allowing an extracting solvent capable of dissolving the polychlorinated biphenyls to be supplied to, and passed through, the alumina layer, and
- securing the extracting solvent passed through the alumina layer.

10. A method for analyzing polychlorinated biphenyls in an oily liquid containing the polychlorinated biphenyls, comprising the steps of:
- adding a sample collected from the oily liquid to a sulfuric acid silica gel layer,
- allowing the sulfuric acid silica gel layer to which the sample is added to be kept in a state heated to at least 35° C. for a predetermined period and then cooling the layer to ordinary temperature,
- supplying an aliphatic hydrocarbon solvent to the sulfuric acid silica gel layer cooled to ordinary temperature,
- allowing the aliphatic hydrocarbon solvent passed through the sulfuric acid silica gel layer to be supplied to, and passed through, a layer of a purifying agent according to claim 1,
- allowing the aliphatic hydrocarbon solvent passed through the purifying agent layer to be supplied to, and passed through, an alumina layer,
- allowing an extracting solvent capable of dissolving the polychlorinated biphenyls to be supplied to, and passed through, the alumina layer,
- securing the extracting solvent passed through the alumina layer, and
- analyzing the secured extracting solvent by either one among gas chromatography and bioassay.

* * * * *